US005693460A

United States Patent [19]

Lok

[11] Patent Number: 5,693,460

[45] Date of Patent: *Dec. 2, 1997

[54] SILVER HALIDE PHOTOGRAPHIC ELEMENTS CONTAINING DIOXIDE COMPUNDS A STABILIZERS

[75] Inventor: Roger Lok, Rochester, N.Y.

[73] Assignee: Eastman Kodak Company, Rochester, N.Y.

[ * ] Notice: The term of this patent shall not extend beyond the expiration date of Pat. No. 5,670,307.

[21] Appl. No.: 668,757

[22] Filed: Jun. 24, 1996

[51] Int. Cl.$^6$ .......................... G03C 1/34; G03C 1/1015; C07D 327/04; C07D 339/02

[52] U.S. Cl. .......................... 430/611; 430/569; 430/600; 430/603; 430/614; 430/615; 548/153; 548/218; 548/259; 548/360.5; 549/31; 549/33; 549/36; 549/35; 546/82; 546/114; 544/235; 544/255; 544/345; 544/350

[58] Field of Search .................................... 430/614, 613, 430/611, 569, 573, 606, 607, 600, 603, 615; 549/31, 33, 36; 548/153, 218, 259, 360.5; 546/114, 82; 544/235, 255, 345, 350

[56] References Cited

U.S. PATENT DOCUMENTS 5,003,097 3/1991 Beaucage et al. ...................... 558/129
5,066,573 11/1991 Matushita et al. ...................... 430/600
5,116,723 5/1992 Kajiwara et al. ...................... 430/611
5,219,721 6/1993 Klaus et al. ........................... 430/569

FOREIGN PATENT DOCUMENTS 4-019736 1/1992 Japan .................................... 430/603

OTHER PUBLICATIONS

OPPI Briefs, vol. 24, No. 4, pp. 488–492, 1992.

*Primary Examiner*—Richard L. Schilling
*Attorney, Agent, or Firm*—Sarah Meeks Roberts

[57] ABSTRACT

This invention provides a silver halide photographic element comprising a silver halide emulsion in reactive association with a dioxide compound represented by the following formula:

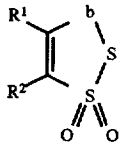

wherein b is C(O), C(S), C(Se), CH2 or (CH2)2; and $R^1$ and $R^2$ are independently H, or aliphatic, aromatic or heterocyclic groups, or $R^1$ and $R^2$ together represent the atoms necessary to form a five or six-membered ring or a multiple ring system. This invention further provides a method of making silver halide emulsions containing the dioxide compounds.

20 Claims, No Drawings

SILVER HALIDE PHOTOGRAPHIC ELEMENTS CONTAINING DIOXIDE COMPUNDS A STABILIZERS

FIELD OF THE INVENTION

This invention relates to the use of certain dioxide compounds as stabilizers in silver halide photographic elements and the preparation of silver halide emulsions containing the dioxide compounds.

BACKGROUND OF THE INVENTION

Problems with fogging have plagued the photographic industry from its inception. Fog is a deposit of silver or dye that is not directly related to the image-forming exposure, i.e., when a developer acts upon an emulsion layer, some reduced silver is formed in areas that have not been exposed to light. Fog can be defined as a developed density that is not associated with the action of the image-forming exposure, and is usually expressed as "D-min", the density obtained in the unexposed portions of the emulsion. Density, as normally measured, includes both that produced by fog and that produced as a function of exposure to light. It is known in the art that the appearance of photographic fog related to intentional or unintentional reduction of silver ion (reduction sensitization) can occur during many stages of preparation of the photographic element including silver halide emulsion preparation, spectral/chemical sensitization of the silver halide emulsion, melting and holding of the liquid silver halide emulsion melts, subsequent coating of silver halide emulsions, and prolonged natural and artificial aging of coated silver halide emulsions. The chemicals used for preventing fog growth as a result of aging or storage are generally known as emulsion stabilizers.

The control of fog, whether occurring during the formation of the light-sensitive silver halide emulsion, during the spectral/chemical sensitization of those emulsions, during the preparation of silver halide compositions prior to coating on an appropriate support, or during the aging of such coated silver halide compositions, has been attempted by a variety of means. Mercury-containing compounds, such as those described in U.S. Pat. Nos. 2,728,663; 2,728,664; and 2,728,665, have been used as additives to control fog. Thiosulfonates and thiosulfonate esters, such as those described in U.S. Pat. Nos. 2,440,206; 2,934,198; 3,047,393; and 4,960,689, have also been employed. Organic dichalcogenides, for example, the disulfide compounds described in U.S. Pat. Nos. 1,962,133; 2,465,149; 2,756,145; 2,935,404; 3,184,313; 3,318,701; 3,409,437; 3,447,925; 4,243,748; 4,463,082; and 4,788,132 have been used not only to prevent formation of fog but also as desensitizers and as agents in processing baths and as additives in diffusion transfer systems. Organic compounds having a polysulfur linkage comprised of three or more sulfur atoms, and organic compounds having a heterocyclic ring having at least two thioether linkages or at least one disulfur linkage, such as those described in U.S. Pat. No. 5,116,723, in combination with nitrogen-containing cyclic compounds have also been discussed as suppressing fog and improving raw stock stability.

Despite the vast amount of effort which has gone into methods to control fog in photographic elements there is a continuing need in the industry for practical and environmentally benign stabilizers which do not otherwise adversely affect the performance of the photographic element.

SUMMARY OF THE INVENTION

This invention provides a silver halide photographic element comprising a silver halide emulsion in reactive association with a dioxide compound represented by the following formula:

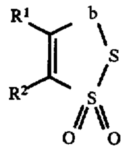

wherein b is C(O), C(S), C(Se), CH2 or (CH2)2; and $R^1$ and $R^2$ are independently H, or aliphatic, aromatic or heterocyclic groups, or $R^1$ and $R^2$together represent the atoms necessary to form a five or six-membered ring or a multiple ring system In one embodiment, the silver halide emulsion is greater than 90 mole % silver chloride. This invention also provides a method of making a silver halide emulsion comprising the dioxide compounds described above.

The silver halide photographic elements of this invention exhibit reduced fog. The dioxide compounds used in this invention are commercially available and easy to handle. Further, they may be used in combination with other antifoggants and stabilizers and they may be added at any stage of the preparation of the emulsion.

DETAILED DESCRIPTION OF THE INVENTION

It is understood throughout this specification and claims that any reference to a substituent by the identification of a group containing a substitutable hydrogen (e.g., alkyl, amine, aryl, alkoxy, heterocyclic, etc.), unless otherwise specifically described as being unsubstituted or as being substituted with only certain substituents, shall encompass not only the substituent's unsubstituted form but also its form substituted with any substituents which do not negate the advantages of this invention.

The compounds of this invention are dioxide compounds represented by Formula I:

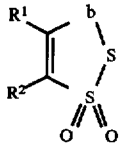

(I)

b is C(O), C(S), C(Se), CH2 or (CH2)2; more preferably b is C(O), C(S), or C(Se) with C(O) being most preferred.

$R^1$ and $R^2$ can be any substituents which are suitable for use in a silver halide photographic element and which do not interfere with the stabilizing activity of the dioxide compound. $R^1$ and $R^2$ may be independently H, or a substituted or unsubstituted aliphatic, aromatic, or heterocyclic group or $R^1$ and $R^2$ together represent the atoms necessary to form a ring or a multiple ring system.

When $R^1$ and $R^2$ are aliphatic groups, preferably, they are alkyl groups having from 1 to 22 carbon atoms, or alkenyl or alkynyl groups having from 2 to 22 carbon atoms. More preferably, they are alkyl groups having 1 to 8 carbon atoms, or alkenyl or alkynyl groups having 3 to 5 carbon atoms. These groups may or may not have substituents. Examples of alkyl groups include methyl, ethyl, propyl, butyl, pentyl, hexyl, octyl, 2-ethylhexyl, decyl, dodecyl hexadecyl, octadecyl, cyclohexyl, isopropyl and t-butyl groups. Examples of alkenyl groups include allyl and butenyl groups and examples of alkynyl groups include propargyl and butynyl groups.

The preferred aromatic groups have from 6 to 20 carbon atoms and include, among others, phenyl and naphthyl groups. More preferably, the aromatic groups have 6 to 10 carbon atoms. These groups may have substituent groups. The heterocyclic groups are 3 to 15-membered rings with at least one atom selected from nitrogen, oxygen, sulfur, selenium and tellurium. More preferably, the heterocyclic groups are 5 to 6-membered rings with at least one atom selected from nitrogen. Examples of heterocyclic groups include pyrrolidine, piperidine, pyridine, tetrahydrofuran, thiophene, oxazole, thiazole, imidazole, benzothiazole, benzoxazole, benzimidazole, selenazole, benzoselenazole, tellurazole, triazole, benzotriazole, tetrazole, oxadiazole, or thiadiazole rings.

Preferably, $R^1$ and $R^2$ together form a ring or multiple ring system. The ring and multiple ring systems formed by $R^1$ and $R^2$ may be alicyclic or they may be the aromatic and heterocyclic groups described above. In a preferred embodiment, $R^1$ and $R^2$ together form a 5 or 6-membered ring, preferably, an aromatic ring. Most preferably, the dioxide compound is 3H-1,2-benzodithiol-3-one-1,1-dioxide (Compound A).

Nonlimiting examples of substituent groups for $R^1$ and $R^2$ include alkyl groups (for example, methyl, ethyl, hexyl), alkoxy groups (for example, methoxy, ethoxy, octyloxy), aryl groups (for example, phenyl, naphthyl, tolyl), hydroxy groups, halogen atoms, aryloxy groups (for example, phenoxy), alkylthio groups (for example, methylthio, butylthio), arylthio groups (for example, phenylthio), acyl groups (for example, acetyl, propionyl, butyryl, valeryl), sulfonyl groups (for example, methylsulfonyl, phenylsulfonyl), acylamino groups, sulfonylamino groups, acyloxy groups (for example, acetoxy, benzoxy), carboxyl groups, cyano groups, sulfo groups, and amino groups. Preferred substituents are lower alkyl and alkoxy groups (for example, methyl and methoxy).

Specific examples of the dioxide compounds include, but are not limited to:

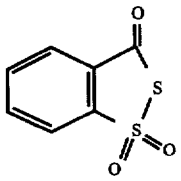
A

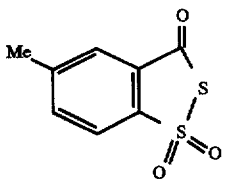
B

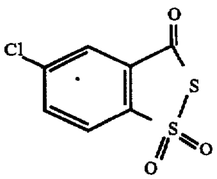
C

-continued

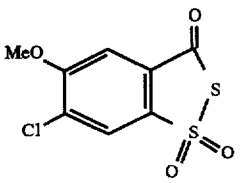
D

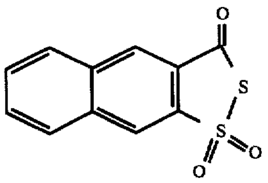
E

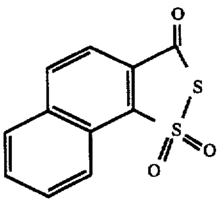
F

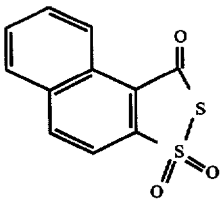
G

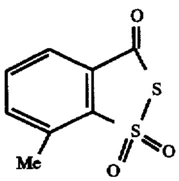
H

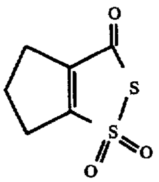
I

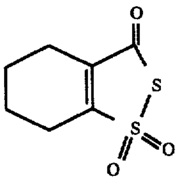
J

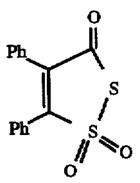
K

-continued
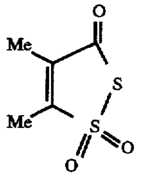
L
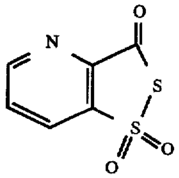
M
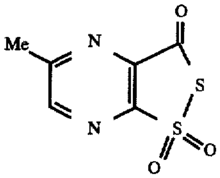
N
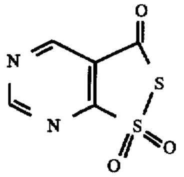
O
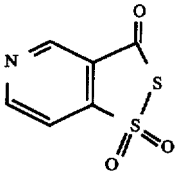
P
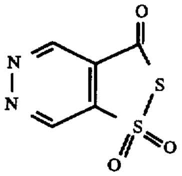
Q
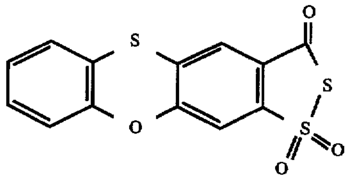
R
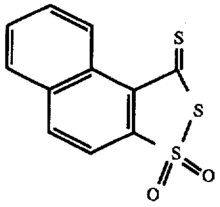
S
-continued
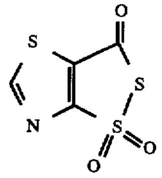
T
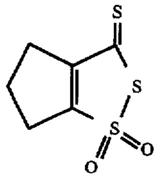
U
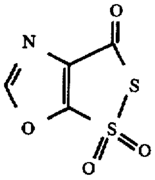
V
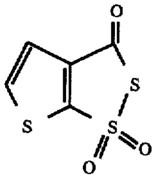
X
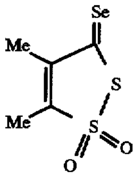
Y
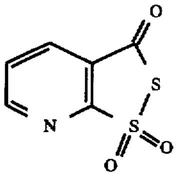
Z
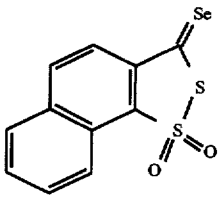
A1
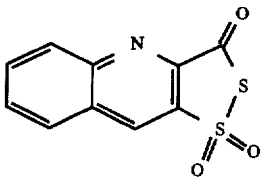
B1

-continued

C1

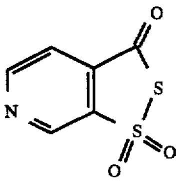

D1

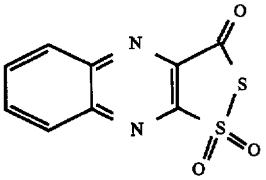

E1

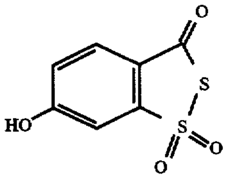

F1

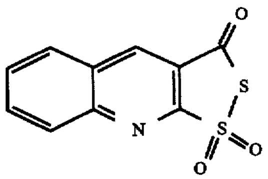

G1

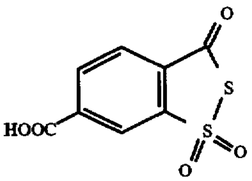

H1

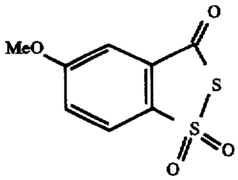

I1

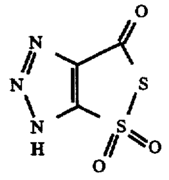

J1

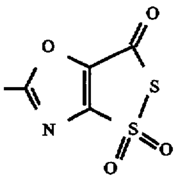

-continued

K1

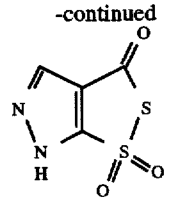

L1

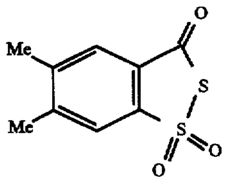

M1

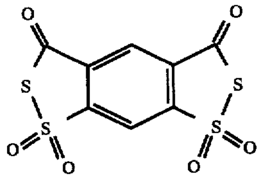

One method of preparing an aromatic 3H-1,2-dithiol-3-one 1,1-dioxide is via the cyclization of an ortho substituted aryl mercaptocarboxylic acid in the presence of thiolacetic acid, followed by oxidation of the product with hydrogen peroxide as described in *OPPI Briefs* 24, #4, 488 (1992), incorporated herein by reference. 3H-1,2-dithiol-3-one 1,1-dioxide may also be prepared as described in U.S. Pat. No. 5,003,097, incorporated herein by reference. Alternatively, this class of compounds may be purchased commercially.

Useful levels of dioxide compounds range from 0.001 mg to 1000 mg per silver mole. The preferred range is from 0.01 mg to 500 mg per silver mole with a more preferred range being from 0.1 mg to 100 mg per silver mole. The most preferred range is from 1 mg to 50 mg per silver mole.

The compounds of this invention may be added to the photographic emulsion using any technique suitable for this purpose. They may be dissolved in most common organic solvents, excluding methanol. Examples of suitable solvents include acetonitrile or acetone. The dioxide compounds can be added to the emulsion in the form of a liquid/liquid dispersion similar to the technique used with certain couplers. They can also be added as a solid particle dispersion.

The dioxide compounds may be added to any layer where they are in reactive association with the silver halide. By "in reactive association with" it is meant that the compounds must be contained in the silver halide emulsion layer or in a layer whereby they can react or interact with the silver halide emulsion. For example, the compounds can also be added to gelatin-only overcoats or interlayers.

The dioxide compounds may be used in addition to any conventional emulsion stabilizer or antifoggant as commonly practiced in the art. Combinations of more than one dioxide compound may be utilized.

The photographic emulsions of this invention are generally prepared by precipitating silver halide crystals in a colloidal matrix by methods conventional in the art. The colloid is typically a hydrophilic film forming agent such as gelatin, alginic acid, or derivatives thereof.

The crystals formed in the precipitation step are washed and then chemically and spectrally sensitized by adding spectral sensitizing dyes and chemical sensitizers, and by providing a heating step during which the emulsion temperature is raised, typically from 40° C. to 70° C., and maintained for a period of time. The precipitation and spectral and chemical sensitization methods utilized in preparing the emulsions employed in the invention can be those methods known in the art.

Chemical sensitization of the emulsion typically employs sensitizers such as: sulfur-containing compounds, e.g., allyl isothiocyanate, sodium thiosulfate and allyl thiourea; reducing agents, e.g., polyamines and stannous salts; noble metal compounds, e.g., gold, platinum; and polymeric agents, e.g., polyalkylene oxides. As described, heat treatment is employed to complete chemical sensitization. Spectral sensitization is effected with a combination of dyes, which are designed for the wavelength range of interest within the visible or infrared spectrum. It is known to add such dyes both before and after heat treatment.

After spectral sensitization, the emulsion is coated on a support. Various coating techniques include dip coating, air knife coating, curtain coating and extrusion coating.

The compounds of this invention may be added to the silver halide emulsion at any time during the preparation of the emulsion, i.e., during precipitation, during or before chemical sensitization or during final melting and co-mixing of the emulsion and additives for coating. Most preferably, these compounds are added during or after chemical sensitization.

The silver halide emulsions utilized in this invention may be comprised of any halide distribution. Thus, they may be comprised of silver chloride, silver bromide, silver bromochloride, silver chlorobromide, silver iodochloride, silver iodobromide, silver bromoiodochloride, silver chloroiodobromide, silver iodobromochloride, and silver iodochlorobromide emulsions. It is preferred, however, that the emulsions be predominantly silver chloride emulsions. By predominantly silver chloride, it is meant that the grains of the emulsion are greater than about 50 mole percent silver chloride. Preferably, they are greater than about 90 mole percent silver chloride; and optimally greater than about 95 mole percent silver chloride.

The silver halide emulsions can contain grains of any size and morphology. Thus, the grains may take the form of cubes, octahedrons, cubooctahedrons, or any of the other naturally occurring morphologies of cubic lattice type silver halide grains. Further, the grains may be irregular such as spherical grains or tabular grains. Grains having a tabular or cubic morphology are preferred.

The compounds of this invention are particularly useful with intentionally or unintentionally reduction sensitized emulsions. As described in *The Theory of the Photographic Process*, Fourth Edition, T. H. James, Macmillan Publishing Company, Inc., 1977 pages 151–152, reduction sensitization has been known to improve the photographic sensitivity of silver halide emulsions. While reduction sensitized silver halide emulsions generally exhibit good photographic speed they often suffer from undesirable fog and poor storage stability.

Reduction sensitization can be performed intentionally by adding reduction sensitizers, chemicals which reduce silver ions to form metallic silver atoms, or by providing a reducing environment such as high pH (excess hydroxide ion) and/or low pAg (excess silver ion). During precipitation of a silver halide emulsion, unintentional reduction sensitization can occur when, for example, silver nitrate or alkali solutions are added rapidly or with poor mixing to form emulsion grains. Also, precipitation of silver halide emulsions in the presence of ripeners (grain growth modifiers) such as thioethers, selenoethers, thioureas, or ammonia tends to facilitate reduction sensitization.

Examples of reduction sensitizers and environments which may be used during precipitation or spectral/chemical sensitization to reduction sensitize an emulsion include ascorbic acid derivatives; tin compounds; polyamine compounds; and thiourea dioxide-based compounds described in U.S. Pat. Nos. 2,487,850; 2,512,925; and British Patent 789,823. Specific examples of reduction sensitizers or conditions, such as dimethylamineborane, stannous chloride, hydrazine, high pH (pH 8–11) and low pAg (pAg 1–7) ripening are discussed by S. Collier in Photographic Science and Engineering, 23,113 (1979). Examples of processes for preparing intentionally reduction sensitized silver halide emulsions are described in EP 0 348934 A1 (Yamashita), EP 0 369491 (Yamashita), EP 0 371388 (Ohashi), EP 0 396424 A1 (Takada), EP 0 404142 A1 (Yamada), and EP 0 435355 A1 (Makino).

The method of this invention is also particularly useful with emulsions doped with Group VIII metals such as iridium, rhodium, osmium, and iron as described in *Research Disclosure,* September 1994, Item 36544, Section I, published by Kenneth Mason Publications, Ltd., Dudley Annex, 12a North Street, Emsworth, Hampshire P010 7DQ, ENGLAND. Additionally, a general summary of the use of iridium in the sensitization of silver halide emulsions is contained in Carroll, "Iridium Sensitization: A Literature Review," Photographic Science and Engineering, Vol. 24, No. 6, 1980. A method of manufacturing a silver halide emulsion by chemically sensitizing the emulsion in the presence of an iridium salt and a photographic spectral sensitizing dye is described in U.S. Pat. No. 4,693,965. In some cases, when such dopants are incorporated, emulsions show an increased fresh fog and a lower contrast sensitometric curve when processed in the color reversal E-6 process as described in The British Journal of Photography Annual, 1982, pages 201–203.

The photographic emulsions incorporating the stabilizers may be incorporated into color negative (which includes paper) or reversal photographic elements. Photothermographic elements and direct positive elements containing internal latent image silver halide grains, however, are not specifically contemplated.

The photographic elements may be simple single layer elements or multilayer, multicolor elements. Multicolor elements contain dye image-forming units sensitive to each of the three primary regions of the visible light spectrum. Each unit can be comprised of a single emulsion layer or of multiple emulsion layers sensitive to a given region of the spectrum. The layers of the element, including the layers of the image-forming units, can be arranged in various orders as known in the art.

A typical multicolor photographic element comprises a support bearing a cyan dye image-forming unit comprising at least one red-sensitive silver halide emulsion layer having associated therewith at least one cyan dye-forming coupler; a magenta image-forming unit comprising at least one green-sensitive silver halide emulsion layer having associated therewith at least one magenta dye-forming coupler; and a yellow dye image-forming unit comprising at least one blue-sensitive silver halide emulsion layer having associated therewith at least one yellow dye-forming coupler. The element may contain additional layers, such as filter layers, interlayers, overcoat layers, subbing layers, and the like.

The photographic elements may also contain a transparent magnetic recording layer such as a layer containing magnetic particles on the underside of a transparent support, as in U.S. Pat. Nos. 4,279,945 and 4,302,523. Typically, the element will have a total thickness (excluding the support) of from about 5 to about 30 microns.

In the following Table, reference will be made to (1) *Research Disclosure,* December 1978, Item 17643, (2) *Research Disclosure,* December 1989, Item 308119, and (3) *Research Disclosure,* September 1994, Item 36544, all published by Kenneth Mason Publications, Ltd., Dudley Annex, 12a North Street, Emsworth, Hampshire PO10 7DQ, ENGLAND, the disclosures of which are incorporated herein by reference. The Table and the references cited in the Table are to be read as describing particular components suitable for use in the elements of the invention. The Table and its cited references also describe suitable ways of preparing, exposing, processing and manipulating the elements, and the images contained therein.

| Reference | Section | Subject Matter |
|---|---|---|
| 1 | I, II | Grain composition, |
| 2 | I, II, IX, X, | morphology and |
| | XI, XII, | preparation. Emulsion |
| | XIV, XV | preparation including |
| | I, II, III, IX | hardeners, coating aids, |
| 3 | A & B | addenda, etc. |
| 1 | III, IV | Chemical sensitization and |
| 2 | III, IV | spectral sensitization/ |
| 3 | IV, V | desensitization |
| 1 | V | UV dyes, optical |
| 2 | V | brighteners, luminescent |
| 3 | VI | dyes |
| 1 | VI | Antifoggants and |
| 2 | VI | stabilizers |
| 3 | VII | |
| 1 | VIII | Absorbing and scattering |
| 2 | VIII, XIII, | materials; Antistatic layers; |
| | XVI | matting agents |
| 3 | VIII, IX C | |
| | & D | |
| 1 | VII | Image-couplers and image- |
| 2 | VII | modifying couplers; Dye |
| 3 | X | stabilizers and hue |
| | | modifiers |
| 1 | XVII | Supports |
| 2 | XVII | |
| 3 | XV | |
| 3 | XI | Specific layer arrangements |
| 3 | XII, XIII | Negative working |
| | | emulsions; Direct positive |
| | | emulsions |
| 2 | XVIII | Exposure |
| 3 | XVI | |
| 1 | XIX, XX | Chemical processing; |
| 2 | XIX, XX, | Developing agents |
| | XXII | |
| 3 | XVIII, XIX, | |
| | XX | |
| 3 | XIV | Scanning and digital |
| | | processing procedures |

The photographic elements can be incorporated into exposure structures intended for repeated use or exposure structures intended for limited use, variously referred to as single use cameras, lens with film, or photosensitive material package units.

The photographic elements can be exposed with various forms of energy which encompass the ultraviolet, visible, and infrared regions of the electromagnetic spectrum as well as with electron beam, beta radiation, gamma radiation, x-ray, alpha particle, neutron radiation, and other forms of corpuscular and wave-like radiant energy in either noncoherent (random phase) forms or coherent (in phase) forms, as produced by lasers. When the photographic elements are intended to be exposed by x-rays, they can include features found in conventional radiographic elements.

The photographic elements are preferably exposed to actinic radiation, typically in the visible region of the spectrum, to form a latent image, and then processed to form a visible image, preferably by other than heat treatment. Processing is preferably carried out in the known RA-4™ (Eastman Kodak Company) Process or other processing systems suitable for developing high chloride emulsions.

The following examples illustrate the practice of this invention. They are not intended to be exhaustive of all possible variations of the invention.

EXAMPLES

Example 1

In accordance with the present invention, 0.054 mole of a cubic negative silver chloride emulsion sensitized with a colloidal suspension of aurous sulfide (3.9 mg/Ag mol), a blue spectral sensitizing dye, anhydro-5-chloro-3,3'-di(3-sulfopropyl) naphtho[1,2-d] thiazolothiacyanine hydroxide triethylammonium salt (220 mg/Ag mol), potassium bromide (741 mg/Ag mol) and 1-(3-acetamidophenyl)-5-mercaptotetrazole (68 mg/Ag mol) was treated with a solution of Compound A dissolved in acetone in an amount indicated in Table 1. This emulsion further contained a yellow dye-forming coupler alpha-(4-(4-benzyloxy-phenyl-sulfonyl)phenoxy)-alpha(pivalyl)-2-chloro-5-(gamma-(2,4-di-5-amylphenoxy)butyramido)acetanilide (1.08 $g/m^2$) in di-n-butylphthalate coupler solvent (0.27 $g/m^2$), and gelatin (1.51 $g/m^2$). The emulsion (0.34 g $Ag/m^2$) was coated on a resin coated paper support and a 1.076 $g/m^2$ gel overcoat was applied as a protective layer along with the hardener bis (vinylsulfonyl) methyl ether in an amount of 1.8% of the total gelatin weight. The samples were stored as described hereafter.

The coatings were given a 0.1 second exposure, using a 0–3 step tablet (0.15 increments), with a tungsten lamp designed to stimulate a color negative print exposure source. This lamp had a color temperature of 3000 K, log lux 2.95, and the coatings were exposed through a combination of magenta and yellow filters, a 0.3 ND (Neutral Density) filter, and a UV filter. The processing consisted of color development (45 sec, 35° C.), bleach-fix (45 sec, 35° C.) and stabilization or water wash (90 sec, 35° C.) following by drying (60 sec, 60° C.). The chemistry used in the Colenta processor consisted of the following solutions:

| | |
|---|---|
| <u>Developer:</u> | |
| Lithium salt of sulfonated polystyrene | 0.25 mL |
| Triethanolamine | 11.0 mL |
| N,N-diethylhydroxylamine (85% by wt.) | 6.0 mL |
| Potassium sulfite (45% by wt.) | 0.5 mL |
| Color developing agent (4-(N-ethyl-N-2-methanesulfonyl aminoethyl)-2-methyl-phenylenediaminesesquisulfate monohydrate | 5.0 g |
| Stilbene compound stain reducing agent | 2.3 g |
| Lithium sulfate | 2.7 g |
| Potassium chloride | 2.3 g |
| Potassium bromide | 0.025 g |
| Sequestering agent | 0.8 mL |
| Potassium carbonate | 25.0 g |
| Water to total of 1 liter, pH adjusted to 10.12 | |
| <u>Bleach-fix</u> | |
| Ammonium sulfite | 58 g |
| Sodium thiosulfate | 8.7 g |

-continued

| | |
|---|---|
| Ethylenediaminetetracetic acid ferric ammonium salt | 40 g |
| Acetic acid | 9.0 mL |
| Water to total 1 liter, pH adjusted to 6.2 | |
| Stabilizer | |
| Sodium citrate | 1 g |
| Water to total 1 liter, pH adjusted to 7.2 | |

The data in Table I show the fog density of the blue sensitized coatings kept at 0° F. and the changes in fog density after a one and two week storage at 120° F. Fog is measured as the minimum density (Dmin) above zero.

TABLE I

| Sample | Compound A mg/Ag mol | 0° F. Fog | 1-week ΔFog | 2-week ΔFog |
|---|---|---|---|---|
| 1 (comparison | 0 | 0.064 | 0.020 | 0.080 |
| 2 (invention) | 10 | 0.065 | 0.019 | 0.060 |
| 3 (invention) | 20 | 0.062 | 0.014 | 0.057 |
| 4 (invention) | 100 | 0.062 | 0.015 | 0.064 |

It can be seen in Table I that Samples 2–4 of the present invention have reduced fog growth compared to the control (Sample 1) which does not have the compound of the present invention.

Example 2

A cubic silver chloride negative emulsion was similarly sensitized as in Example 1 except that 0.03% iodide was introduced in the course of the precipitation of the emulsion. Compound A was added to this emulsion as before just prior to coating, and the coatings were stored, exposed and processed as in Example 1.

TABLE II

| Sample | Compound A mg/Ag mol | 0° F. Fog | 1-week ΔFog | 2-week ΔFog |
|---|---|---|---|---|
| 5 (comparison | 0 | 0.103 | 0.033 | 0.107 |
| 6 (invention) | 10 | 0.097 | 0.022 | 0.067 |
| 7 (invention) | 20 | 0.087 | 0.016 | 0.037 |
| 8 (invention) | 100 | 0.082 | 0.019 | 0.074 |
| 9 (invention) | 400 | 0.077 | 0.011 | 0.070 |

It can be seen in Table II that the antifogging benefits of the compound of the present invention (Simples 6–9) apply equally well to the chloride emulsion with a different halide composition.

Example 3

In another embodiment of the invention, a 0.3 mole cubic negative silver chloride emulsion was sensitized with a colloidal suspension of aurous sulfide (17.6 mg/Ag mol) at 40° C. The emulsion was heated to 65° C. at a rate of 10° C. per 6 minutes and then held at this temperature for 60 minutes. During this time, 1-(3-acetamidophenyl)-5-mercaptotetrazole (298 mg/Ag mol), potassium hexachloroiridate (III) (0.24 mg/Ag mol), potassium bromide (1372 mg/Ag mol), and Compound A dissolved in acetone in an amount indicated in Table 3 were added. The emulsion was cooled back to 40° C. at a rate of 10° C. per 6 minutes, at which time, a red spectral sensitizing dye, anhydro-3-ethyl-9,11-neopentylene-3'-(3-sulfopropyl)thiadicarbocyanine hydroxide (22 mg/Ag mol), was added and the pH of the emulsion adjusted to 6.0. The emulsion thus sensitized, and also containing a cyan dye-forming coupler 2-(alpha (2,4-di-tert-amylphenoxy)butyramido)-4,6-dichloro-5-ethyl phenol (0.42 $g/m^2$) in di-n-butyl phthalate coupler solvent (0.429 $g/m^2$) was coated on a resin coated paper support and a 1076 $g/m^2$ gel overcoat was applied as a protective layer along with the hardener bis (vinylsulfonyl) methyl ether in an amount of 1.8% of the total gelatin weight. These coatings were stored, exposed and processed as in Example 1.

The data in Table III show that Samples 11–13, containing the compound of the present invention, show a much reduced fog level when compared to Sample 10 without Compound A. Thus it appears that the compounds of this invention are advantageous in controlling fog growth regardless of how the emulsion is spectrally (blue or red) sensitized.

TABLE III

| Sample | Compound A mg/Ag mol | 0° F. Fog | 1-week ΔFog | 2-week ΔFog |
|---|---|---|---|---|
| 10 (comparison) | 0 | 0.12 | 0.037 | 0.158 |
| 11 (invention) | 4 | 0.12 | 0.017 | 0.081 |
| 12 (invention) | 12 | 0.12 | 0.000 | 0.019 |
| 13 (invention) | 20 | 0.12 | 0.011 | 0.053 |

Example 4

The emulsion for this example was prepared as in Example 3 except that Compound A was added at 40° C. after the pH adjustment and the addition of the red sensitizing dye.

TABLE IV

| Sample | Compound A mg/Ag mol | 0° F. Fog | 1-week ΔFog | 2-week ΔFog |
|---|---|---|---|---|
| 14 (comparison | 0 | 0.12 | 0.044 | 0.166 |
| 15 (invention) | 2 | 0.12 | 0.029 | 0.123 |
| 16 (invention) | 4 | 0.12 | 0.025 | 0.109 |
| 17 (invention) | 12 | 0.12 | 0.004 | 0.030 |
| 18 (invention) | 20 | 0.13 | 0.005 | 0.032 |

It is clear from data in Table IV that Compound A is equally effective when added just prior to coating or during the sensitizing process in a red spectrally sensitized emulsion.

The invention has been described in detail with particular reference to the preferred embodiments thereof, but it will be understood that variations and modifications can be effected within the scope of the invention.

What is claimed is:

1. A silver halide photographic element comprising a silver halide emulsion in reactive association with a dioxide compound represented by the following formula:

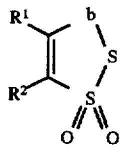

wherein b is C(O), C(S), C(Se), CH2 or (CH2)2; and $R^1$ and $R^2$ are independently H, or aliphatic, aromatic or heterocyclic groups, or $R^1$ and $R^2$ together represent the atoms necessary to form a five or six-membered ring or a multiple ring system.

2. The silver halide photographic element of claim 1 wherein b is C(O), C(S) or C(Se).

3. The silver halide photographic element of claim 2 wherein $R^1$ and $R^2$ together represent the atoms necessary to form a five or six-membered ring or a multiple ring system.

4. The silver halide photographic element of claim 3 wherein $R^1$ and $R^2$ together represent the atoms necessary to form a five or six-membered ring and b is C(O).

5. The silver halide photographic element of claim 4 wherein the dioxide compound is 3H-1,2-benzodithiol-3-one-1,1-dioxide.

6. The silver halide photographic element of claim 1 wherein the silver halide emulsion is greater than 90 mole % silver chloride.

7. The silver halide photographic element of claim 3 wherein the silver halide emulsion is greater than 90 mole % silver chloride.

8. The silver halide photographic element of claim 4 wherein the silver halide emulsion is greater than 90 mole % silver chloride.

9. The silver halide photographic element of claim 1 wherein the concentration of the dioxide compound is from 0.1 to 100 mg/mol Ag.

10. The silver halide photographic element of claim 4 wherein the concentration of the dioxide compound is from 0.1 to 100 mg/mol Ag.

11. A method of making a silver halide emulsion comprising precipitating and chemically sensitizing the emulsion and further comprising adding to the emulsion a compound represented by the following formula:

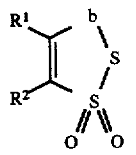

wherein b is C(O), C(S), C(Se), CH2 or (CH2)2; and $R^1$ and $R^2$ are independently H, or aliphatic, aromatic or heterocyclic groups, or $R^1$ and $R^2$ together represent the atoms necessary to form a five or six-membered ring or a multiple ring system.

12. The method of claim 11 wherein b is C(O), C(S) or C(Se).

13. The method of claim 12 wherein $R^1$ and $R^2$ together represent the atoms necessary form a five or six-membered ring or a multiple ring system.

14. The method of claim 13 wherein $R^1$ and $R^2$ together represent the atoms necessary to form a five or six-membered ring and b is C(O).

15. The method of claim 14 wherein the dioxide compound is 3H-1,2-benzodithiol-3-one-1,1-dioxide.

16. The method of claim 11 wherein the silver halide emulsion is greater than 90 mole % silver chloride.

17. The method of claim 13 wherein the silver halide emulsion is greater than 90 mole % silver chloride.

18. The method of claim 14 wherein the silver halide emulsion is greater than 90 mole % silver chloride.

19. The method of claim 11 wherein the amount of the dioxide compound added is from 0.1 to 100 mg/mol Ag.

20. The method of claim 14 wherein the amount of the dioxide compound added is from 0.1 to 100 mg/mol Ag.

* * * * *

UNITED STATES PATENT AND TRADEMARK OFFICE

CERTIFICATE OF CORRECTION

PATENT NO. : 5,693,460

DATED : December 2, 1997

INVENTOR(S) : Roger Lok

It is certified that error appears in the above-identified patent and that said Letters Patent is hereby corrected as shown below:

Col. 1, [54]

delete "COMPUNDS A" and insert -- COMPOUNDS AS --

Signed and Sealed this

Fifth Day of January, 1999

*Attest:*

*Attesting Officer*

*Acting Commissioner of Patents and Trademarks*